(12) United States Patent
McGovern et al.

(10) Patent No.: US 6,971,972 B1
(45) Date of Patent: Dec. 6, 2005

(54) METHOD FOR ENHANCING COMPLIANCE OF HOME-BASED PHYSICAL THERAPY REGIMEN

(76) Inventors: Thomas P. McGovern, 424 S. Spring Ave., LaGrange, IL (US) 60525; Steven L. Mayes, 2775 Patten Ave., Geneva, IL (US) 60134

( * ) Notice: Subject to any disclaimer, the term of this patent is extended or adjusted under 35 U.S.C. 154(b) by 0 days.

(21) Appl. No.: 10/990,602

(22) Filed: Nov. 17, 2004

(51) Int. Cl.⁷ ............................................. A63B 21/00
(52) U.S. Cl. .................... 482/3; 482/1; 482/8; 482/900
(58) Field of Search ........................ 482/1–9, 900–902

(56) References Cited

U.S. PATENT DOCUMENTS

| | | | |
|---|---|---|---|
| 4,278,095 A | 7/1981 | Lapeyre | |
| 5,949,951 A | 9/1999 | Sklar et al. | |
| 5,984,684 A | 11/1999 | Brostedt et al. | |
| 6,007,459 A * | 12/1999 | Burgess | 482/4 |
| 6,371,123 B1 | 4/2002 | Stark et al. | |
| 6,453,111 B1 | 9/2002 | Sklar et al. | |
| 6,567,536 B2 | 5/2003 | McNitt et al. | |
| 6,626,800 B1 | 9/2003 | Casler | |
| 6,786,730 B2 | 9/2004 | Bleckley et al. | |
| 6,808,472 B1 * | 10/2004 | Hickman | 482/8 |
| 6,827,670 B1 * | 12/2004 | Stark et al. | 482/9 |
| 2002/0082143 A1 | 6/2002 | Leeds | |
| 2003/0221687 A1 | 12/2003 | Kaigler | |

* cited by examiner

Primary Examiner—Glenn E. Richman
(74) Attorney, Agent, or Firm—Meroni & Meroni PC.; Christoper J. Scott; Charles F. Meroni, Jr.

(57) ABSTRACT

A methodology is disclosed for providing a physical therapy practitioner with practice-specific prescriptive exercise routine depictions as an effective way to enhance compliance of a home-based physical therapy regimen. The method comprises various steps, including assessing a given practitioner's commonly prescribed home-based exercise prescriptions, selecting certain of the exercises for comparison relative to a previously compiled digitized motion picture library containing excerpts showing various exercises. A decision is then made as to whether a representative exercise excerpt is endemic to the physical therapy practitioner. If the excerpt(s) are deemed satisfactory, DVD's are developed and provided to the practitioner. The practitioner may then properly prescribe a home-based physical therapy regimen during an office visit at which time a select set of the developed DVD materials are delivered to the patient. The practice-specific compilations may be periodically updated to reflect ongoing changes or requirements of a given therapist's practice.

22 Claims, 1 Drawing Sheet

METHOD FOR ENHANCING COMPLIANCE OF HOME-BASED PHYSICAL THERAPY REGIMEN

BACKGROUND OF THE INVENTION

1. Field of the Invention

The present invention generally relates to a method for enhancing compliance of home-based physical therapy exercises. More particularly, the present invention concerns certain procedures for customizing motion picture type demonstrations of exercise routines according to the practices of a given physical therapy practitioner, it being noted that each physical therapy practitioner plies his or her profession in a unique manner. By providing physical therapy practitioners with customized motion picture demonstrations of exercise routines tailored to the practice methods of the practitioner, it is contemplated that patient compliance of prescriptive exercise routines is enhanced.

2. Description of the Prior Art

Physical therapy has its origins in antiquity; certain therapeutic techniques have been recognized and implemented for centuries as a means to improve the physical health of a patient. However, while various physical therapy techniques have ancient origins, the modern profession of physical therapy developed in the twentieth century in the wake of World War I. The very first modern American physical therapists were trained to work with soldiers returning from the war, and several groups of so-called "reconstruction aides" were sent to military hospitals in France to institute early rehabilitation with wounded veterans. The modern day physical therapist practices his or her profession in a wide variety of settings, with patients from all age groups. Commonly, physical therapists are thought of as those who help patients with orthopedic problems, such as low back pain or knee surgeries, to reduce pain and regain function. Other common functions of the physical therapist include providing treatment to assist patients recovering from a stroke in learning how to regain proper use of their limbs. In any event, modern physical therapists are experts in the examination and treatment of musculoskeletal and neuromuscular problems that affect the physical ability of the patient to properly move and otherwise function in the patient's everyday life.

Undeniably, the ability to maintain an upright posture and to move one's arms and legs to perform all sorts of tasks and activities is an important component of one's health. Most people can learn to live with the various medical conditions that they may develop. However, effectively learning to live with various medical conditions requires that people also continue with their careers, support their families, and otherwise enjoy important occasions with family and friends. All of these activities are more readily enjoyable, and thus the quality of life is generally enhanced, if physical movement is made relatively pain-free or if the difficulty therewith is otherwise removed.

For many, the ability to move is not merely a matter of using limbs to walk or handle objects. There are cardiac and pulmonary problems that interfere with the body's ability to use oxygen, which is the "fuel" of muscles and movement. Because people of all ages, from the newborn to the very aged, have the need to move and function, physical therapists work with patients across the lifespan. Physical therapists typically ply their profession in hospitals (even critically ill patients in the intensive care unit), in nursing homes, in outpatient clinics, in the home, in schools, and on the job. Notably, because physical therapists are experts in movement and function, they do not confine their talents to treating people who are ill.

A large part of a physical therapist's program is directed at preventing injury and loss of movement. In this regard, physical therapists work as consultants in industrial settings to improve the design of the workplace and reduce the risk of workers overusing certain muscles or developing low back pain. They also provide services to athletes at all levels to screen for potential problems and institute preventive exercise programs. With the boom in the fitness industry, a number of physical therapists are engaged in consulting with individuals and fitness clubs to develop workouts that are safe and effective, especially for people who already know that they have a problem with their joints or their backs.

Because physical therapists are required to understand a vast array of problems that can affect movement, function, and health, all physical therapists are college graduates. The majority of physical therapist education programs graduate students with a master's degree, and a few schools offer a clinical doctorate in physical therapy. All physical therapists also are required to take a national examination and be licensed by the state in which they practice. Some physical therapists seek advanced certification in a clinical specialty, such as orthopedic, neurologic, cardiopulmonary, pediatric, geriatric, or sports physical therapy. Others are certified in electrophysiological testing and measurement.

The cornerstones of physical therapist treatment are therapeutic exercise and functional training. In addition to "hands-on" care, physical therapists also educate patients to take care of themselves and to perform certain exercises on their own. Depending on the particular needs of a patient, physical therapists may also "mobilize" or "manipulate" a joint (that is, perform certain types of movements at the end of one's range of motion) or massage a muscle to promote proper movement and function. Physical therapists also use methods such as ultrasound (which uses high frequency waves to produce heat), hot packs, and ice. Although other kinds of practitioners will offer some of these treatments as "physical therapy," it is important to note that physical therapy can only be provided by qualified physical therapists or by physical therapist assistants, who must complete a 2-year education program and who work only under the direction and supervision of physical therapists.

Finding the right physical therapist is much like finding the right doctor, dentist, or lawyer. In this regard, word-of-mouth recommendations from family or friends frequently provide seekers of physical therapy services with some guidance as to the right kind of physical therapy practitioner for a given patient. In a hospital setting, by way of contrast, a physical therapist will likely pick up a patient's case much the same way as a physician. For outpatient care, physical therapy can be obtained through hospitals, home care agencies, and in private offices. One may also easily find a physical therapist's office listed in the phone book.

Many physical therapists are members of their voluntary professional association, the American Physical Therapy Association (APTA). These physical therapists and their physical therapist assistants are especially committed to providing competent and compassionate care, as they are bound by the Association's Code of Ethics. It will thus be understood that physical therapists are professionals, and as such, develop physical therapy practices under or within the guidelines of an ethical code. Physical therapy practices are thus often dynamic in character and often differ markedly from clinic to clinic and from therapist to therapist. In view of the fact that physical therapists continue to develop practices unique to the therapeutic philosophies endemic to a given therapeutic setting, it will be further understood that physical therapy regimens often differ from one setting to another. It is with these notions in mind that the methodologies of the present invention have been developed. Notably, the patient is at the center of any prescription for physical therapy and thus the patient has individualized physical therapy requirements. Various types of methodologies have been developed in an effort to enhance the care and well-being of patients in need of physical therapy. Some of the more pertinent prior art relating to physical therapy methodology and the like is described hereinafter.

U.S. Pat. No. 4,278,095 ('095 patent), which issued to Lapeyre, discloses an Exercise Monitor System and Method. The '095 patent teaches certain methodology for encouraging optimal exercise, particularly of the aerobic type, for cardiovascular fitness. The user powers an exerciser, such as a treadmill, simulated cycling or rowing, and the like, and a monitor displays the user's speed and distance accomplished. A variable speed outdoor exercising scene (such as a person rowing a boat) is shown to the user when the monitor is a TV set. The users speed signal controls the speed of a videotape cassette player to proportionately change the speed of the outdoor exercising scene. The speed signal is converted to the reciprocal of speed i.e., minutes per mile and the distance is displayed to hundredths of miles. The latter two signals are converted to BCD digits and superimposed on the video through a TV positioning and generation circuit for display on the scene. The heartbeat is picked up electrically or by infra red and converted into three digits of beats per minute, and also superimposed on the video for display on the monitor. In addition, the user's pulse or heart rate is displayed.

U.S. Pat. No. 5,949,951 ('951 patent) and U.S. Pat. No. 6,453,111 ('111 Patent), which issued to Sklar et al., disclose Interactive Workstation(s) for Creating Customized, Watch and Do Physical Exercise Programs. The '951 and '111 Patents thus teach interactive touch screen workstations for generating patient-specific physical therapy videotapes. The workstations generally include an appropriately programmed, digital central processing unit; first storage means for storing digital video exercise data; second storage means for storing digital audio exercise data; third storage means for storing digital patient data; fourth storage means for storing digital audio music data; user interface controls for directing the operation of the central processing unit so as to (i) generate a sequence of digital video frames from the data contained in the first storage means, with that sequence corresponding to a particular physical therapy regimen prescribed for that patient, and (ii) generate a digital audio track from the digital audio exercise data contained in the second storage mean, and/or the digital audio music data contained in the fourth storage means, with the digital audio track generated by the central processing unit corresponding to the sequence of digital video frames generated by the central processing unit; and output means for recording the sequence of digital video frames generated by the central processing unit and digital audio track generated by the central processing unit on a standard videotape, which videotape can thereafter be used by a patient to conduct "watch-and-do" physical therapy by playing back the videotape while simultaneously carrying out the regimen of physical therapy exercises specified in, and illustrated by, that same videotape.

U.S. Pat. No. 6,007,459 ('459 patent), which issued to Burgess, discloses a Method and System for Providing Physical Therapy Exercises. The '459 patent teaches a method and system for providing physical therapy to a human client having a physical condition including the steps of providing an electronic communication link between the client and a therapist, instructing the client to move in a particular manner, or to assume a sustained posture or perform a test. Then, feedback is requested from the client. The feedback relates to bodily sensation corresponding to the movement or sustained posture and can be audio, video, and/or data type feedback. The communication link communicates the feedback to the therapist. Accordingly, the therapist utilizes the feedback to assess the physical condition of the client. The therapist also communicates remedial movements or a remedial sustained posture to the client to address the physical condition. Various postural measurements and testing devices are used in conjunction with the present invention to facilitate assessment and help address the physical condition in accordance with accepted physical therapy techniques.

U.S. Pat. No. 6,371,123 ('123 patent), which issued to Start et al., discloses a System for Orthopedic Treatment Protocol and Method of Use Thereof. The '123 patent teaches a process for treating orthopedic injuries including the steps of presenting a set of treatment protocols; approving a treatment protocol from among the presented set of treatment protocols; capturing information identifying the approved treatment protocol from among the set of presented protocols; and generating information from the captured information into a form compatible with a handheld computer adapted for connection to an orthopedic sensor system. The generated information includes parameters of the identified approved treatment protocol. The process may also include the steps of basing the presented set of treatment protocols upon a database of historic patients, orthopedic injuries, treatment protocols and outcomes, and retaining information about the current patient, the patient's injury, treatment protocol and outcome.

U.S. Pat. No. 6,567,536 ('536 patent), which issued to McNitt et al., discloses a Method and System for Physical Motion Analysis. The '536 patent teaches an analysis system and method for providing athletic training and instruction by sensing different types of information, such as video, positional information, weight transfer information, etc. and synchronizing the information. The synchronized information is replayed for the user in a manner that enables simultaneous viewing of an athletic motion along with calculations and presentation of analysis information related to the athletic motion.

U.S. Pat. No. 6,626,800 ('800 patent), which issued to Casler, discloses a Method of Exercise Prescription and Evaluation. The '800 patent teaches an exercise method that provides a tailor made exercise protocol that can be modified by a clinician in a supervisory position. A processor with a protocol-generating algorithm is used in communication with an exercise device. Data is input into the processor, such as age, height, weight and sex, and the processor generates an exercise protocol according to a protocol-generating algorithm and the user data. A supervisor is then capable of reviewing and allowing for modification of this exercise protocol. After the exercise protocol is approved it is transferred to the exercise device. A user can then perform an exercise session on the exercise device. Sensors on the device and/or user generate information regarding the exercise session. This information is transferred back to the processor where it is reviewed by the supervisor where the supervisor has the ability to modify the protocol for the next exercise session if they deem it necessary.

United States Patent Application Publication No. 2002/0082143 ('143 Publication), authored by Leeds, discloses a Method and System for Creating Customized Exercise Routines. The '143 Publication thus teaches a method for creating a customized visual presentation of a physical therapy routine comprising various steps. The initial step of evaluating the capability of the individual for performing a given routine is followed by the step of categorizing the individual according to the evaluated performance capability. Based on the category of the individual, the physical therapist identifies a sequence of physical exercises for the individual, which sequence defines the individualized physical therapy routine. The therapist then accesses a digital excerpt archive, which digital excerpts demonstrate the performance of a particular physical exercise. The physical therapist selectively retrieves digital excerpts from the archive that visually demonstrate the physical exercises that will make up the routine. These digital excerpts are edited and provided to the patient via various means, including electronic web-based delivery, hard copy delivery, or machine readable media, such as compact disc or video tape.

As noted by Leeds, physical therapy routines typically consist of a series of physical exercises. They are usually prescribed and assigned to a patient for rehabilitation from a disease and/or injury. Once prescribed, the physical therapist attempts to insure that the patient fully comprehends the exercise prescription and how to properly execute the exercise routine comprising the regimen so that the patient may fulfill his or her physical therapy regimen at home. Many times, the physical therapist demonstrates how to properly execute the exercises and provides photos or two-dimensional illustrations as well as written instructions on how to properly perform exercise routines so that the patient may reference the same if necessary. As Leeds further notes, this type of methodology has often proved ineffectual, particularly if the prescribed routine is lengthy and involved. Notably, even if the patient fully understands how to correctly execute an exercise routine at the time of the appointment, the patient often tends to forget how to correctly perform certain exercises in the routine once the patient attempts to comply with his or her home-based or "at-home" physical therapy regimen.

Many have attempted to enhance home-based compliance of a given physical therapy regimen by providing the physical therapy patient with motion picture type depictions of how to correctly perform exercise routines. Regardless of the medium on which the motion picture type depictions are presented, such depictions are static in nature. In other words, once the exercise routine is captured on a medium, the motion picture depictions are delivered in bulk to physical therapy practitioners (whether physical therapists, physical therapy clinics, or hospital-based, physical-therapy departments) for patient provision without regard to the practice-specific requirements of a given physical therapy practitioner. Furthermore, typically, there is no on-ongoing analysis or periodic review of the motion picture depictions to account for and implement developing physical therapy philosophies and/or theories.

Thus, it will be seen from an inspection of the aforementioned patent disclosures and physical therapy methods otherwise known to exist, that the prior art does not teach physical therapy methodology whereby motion picture depictions are tailor made for physical therapy practitioners, as earlier described. In other words, as earlier noted, physical therapy practitioners practice physical therapy in various ways according to various schools of thought or underlying philosophies and/or theories. Any given static motion picture depiction, while suitable for a first physical therapy practitioner, may not be suitable for a second physical therapy practitioner. It is further contemplated that patients tend to seek out a given physical therapy practitioner for various reasons, not the least of which is to attain some comfort level with the practitioner and the physical therapy practice(s) of that practitioner. Further, it is contemplated that compliance of a given home-based physical therapy regimen is intimately related to the patient's choice of physical therapy practice. In other words, if a patient is well-suited with a given physical therapy practice, the patient's compliance of home-based physical therapy regimen will likely be enhanced. Thus, the underlying theory of the present invention is based on the contention that the success of a patient's physical therapy will depend upon the degree of agreement between the physical therapy patient and the chosen physical therapy practice. It is contemplated that the better the fit (or agreement) is between a given patient and a given practice; the better the compliance will be with a home-based physical therapy regimen. In this regard, it is noted that physical therapy practitioners are highly desirous of providing practice-specific exercise routines for their patients. Thus, the prior art perceives a need for a method of enhancing compliance of home-based physical therapy regimens by providing the physical therapy practitioners with motion picture type depictions tailor made for the given practitioner.

SUMMARY OF THE INVENTION

Thus, it is a primary object of the present invention to provide tailor made motion picture depictions of exercise routines to a given physical therapy practitioner as a means to enhance compliance of a home-based physical therapy regimen. To achieve these and other readily apparent objectives, the present invention essentially discloses certain methodology for providing a physical therapy practitioner with practice-specific prescriptive exercise routine depictions, the practice-specific prescriptive exercise routine depictions for enhancing compliance of a home-based physical therapy regimen. The disclosed methodology essentially comprises the steps of assessing home-based exercise prescriptions, the home-based exercise prescriptions being endemic to a physical therapy practitioner (the home-based exercise prescriptions comprising a plurality of so-called "best-practice" exercises). Further, the method comprises a step of selecting at least one best-practice exercise, the best-practice exercise being selected by the physical therapy practitioner. Further, a representative best-practice exercise excerpt is selected, the representative best-practice exercise excerpt being selected from a previously compiled digitized motion picture library, the digitized motion picture library comprising a plurality of visual best-practice exercise excerpts. A decision is then made as to whether the representative best-practice exercise excerpt or excerpts are endemic to the physical therapy practitioner. If the representative best-practice exercise excerpt(s) are deemed endemic, digital versatile disc materials endemic to the physical therapy practitioner are then developed. After developing the digital versatile disc (DVD) materials, the developed digital versatile disc materials are provided to the physical therapy practitioner. Once the practitioner has sufficient digital versatile disc materials, he or she may then properly prescribe a home-based physical therapy regimen. At the time of the physical therapy appointment with a given patient a select set of developed digital versatile disc materials are delivered to the patient, the select set of developed digital versatile disc materials being designed to effectively enhance compliance of the home-based physical therapy regimen.

Other objects of the present invention, as well as particular features, elements, and advantages thereof, will be elucidated in, or apparent from, the following description and the accompanying drawing FIGURES.

DETAILED DESCRIPTION OF THE PREFERRED EMBODIMENT

Figure 1:
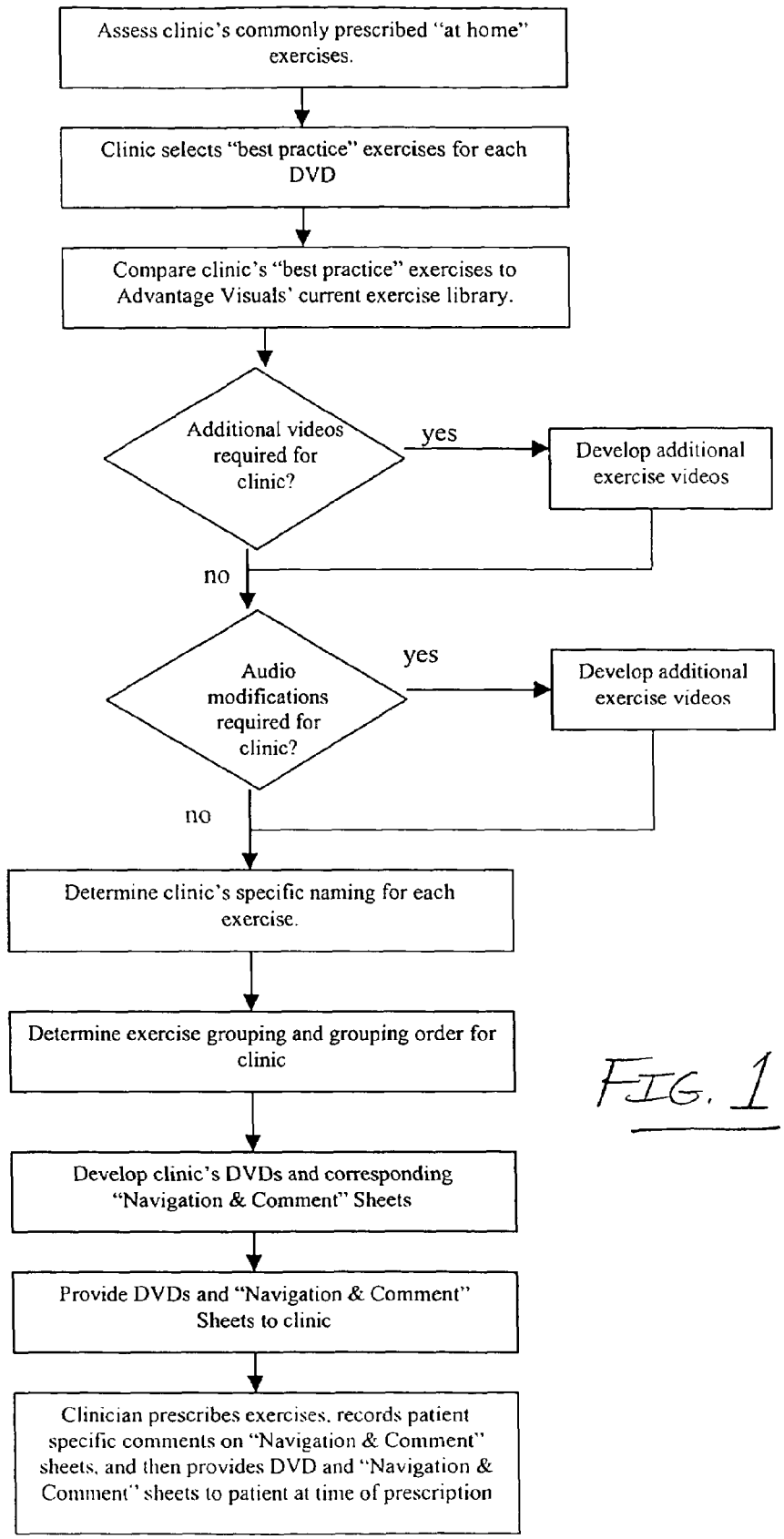
FIG. 1 is a flowchart depicting the main features of the inventive methodologies of the present invention.

Notably, usage of video or motion picture footage is superior to static two-dimension picture(s) for demonstrating physically therapy type exercise routines. The better a patient understands how to perform the exercise routines the more likely it is that the patient will be able to comply with the clinician's or practitioner's prescription in terms of a) the frequency of the patient performing the exercises as well as b) adherence to proper technique. Performance of "at home" or home-based exercise is an integral part of most physical therapy. It is common for the clinician or the practitioner to prescribe "at home" exercises at the initial office visit or appointment. Typically, the exercises are to be performed immediately (within 24 hours) following the first visit. The following defined methodologies allow the clinic/clinician or physical therapy practitioner to provide the patient with a digital versatile disc (DVD) at the time of prescription, rather than have the patient wait a day or more for the DVD to be manufactured and delivered as intimated in the '143 Publication.

Further, the following methodologies require the clinic or physical therapy practitioner to declare their typically prescribed "at home" exercises, and thus the specified methodologies help the clinic(s) or practitioners standardize with regards to the prescribed at home exercises. This standardization has two benefits, namely, 1) because many therapists will have input into the final superset of exercises definition for the clinic, exchange of ideas and experiences will take place which focuses on why one exercise may be better then another exercise, assuming both exercises are intended to achieve the same result. The resulting superset, in essence, represents the clinic's "best practice" exercises, 2) it is common in many clinics for the patient to be treated by different therapists due to scheduling differences. Definition of the superset, which represents the clinic's best practices for at home exercises, increases the treatment compatibility among clinicians working at the same clinic.

It is further noted that physical therapy practitioners, whether solo, clinic-based, or hospital department based, have concern that patients will attempt exercises that have not yet been prescribed in view of the patient's state of physical health. If a patient attempts to perform a non-prescribed exercise for which they are not ready, they increase their risk of injury. Comparatively, there is less risk of injury if the patient performs a less advanced non-prescribed exercise. The present methodology details procedures wherein the DVD's are provided to the clinic or practitioner to segment the exercises on the DVD by groups. A group is a set of exercises typically appropriate for the same point of the patient's progression. Groups are preferably referred to numerically (Group 1, Group 2, etc) or alphabetically (Group A, Group B, etc). The groups are organized such that the exercises associated with the beginning of therapy are included in a low number/letter group. Exercises intended for advanced patients are included in a higher number/letter group. Placing the more advanced exercises further down the grouping reduces the likelihood that a patient will attempt a non-prescribed exercise that is overly advanced.

It will be noted that the foregoing denoted or implies a flat grouping hierarchy. As a means to enhance the foregoing, it is contemplated that multiple levels can be defined to further shield the patient from overly advanced exercises. For example, the initial menu presented could be the A group which provides access to Exercise A1, Exercise A2, Exercise A3, etc. as well as a "B" group menu. The B group menu could provide access to Exercise B1 thru Exercise Bn and then on to Group C. In this example, "C" exercises are more advanced then B exercises, and B exercises are more advanced then "A" exercises. The patient could be required to navigate through "A" exercises and then "B" exercises before obtaining access to the "C" exercises. The digital versatile disc format more easily enables this type of formatting structure and thus the preferred methods as hereinafter specified contemplate use of a digital versatile disc medium or format.

The present invention thus contemplates a method for enhancing compliance of a home-based physical therapy regimen. As earlier noted, it is contemplated that patients are more likely to comply with home-based physical therapy regimen if the patient is able to choose or gravitate into a physical therapy practice that appeals to the patient. Notably, while there are similarities between physical therapy practitioners, each practice or practitioner may subscribe to different physical therapy philosophies and/or theories. The present invention thus attempts to provide practice-specific exercise routine motion picture excerpts as a means to enhance compliance of a home-based physical therapy regimen. In this regard, the method preferably comprises the steps of initially compiling a digitized motion picture library. This step is accomplished by digitally capturing physical therapy experts performing both standard physical therapy exercise routines and practice-specific motion picture type depictions. The resulting motion picture depictions or demonstrations are then electronically archived for future reference and review. It will thus be understood that the digitized motion picture library preferably comprises a plurality of visual so-called "best-practice" exercise excerpts, each of which visually demonstrate or depict a prescriptive physical therapy exercise. In this regard, it is noteworthy that different practitioners may be desirous of obtaining excerpts having various types of actors, backgrounds, and auditory sensory information. The present methodology attempts to accommodate the practice-specific needs and/or desires and is open to providing best-practice exercise excerpts incorporating the practice-specific visual/auditory requirements. Those responsible for capturing the visual/auditory images in digital format (the DVD provider) may thus correspond with various practitioners until a final excerpt style or depiction is agreed upon.

After compiling the digitized motion picture library, the provider of the digital versatile disc materials may then comfortably approach physical therapy practitioners and assess home-based exercise prescriptions for any given physical therapy practitioner. Notably, the home-based exercise prescriptions of a given practitioner are endemic to that physical therapy practitioner and typically comprise a plurality of best-practice exercises, as earlier described. In this regard, it is contemplated that physical therapy practitioners have a practice-specific repertoire of physical exercise routines that may be prescribed for their patients on an as needed basis. This practice-specific repertoire of physical exercise routines may thus be deemed endemic to or characteristic of a given practice setting or practitioner. The repertoire may thus be assessed or otherwise evaluated and defined according to the requirements of the practitioner and the DVD materials provider.

After assessing the home-based exercise prescriptions of a given practitioner, at least one best-practice exercise is selected. In this regard, it is contemplated that in the preferred methodology a number of best-practice exercises may be selected for inclusion in any given physical therapy regimen since physical therapy often involves the prescription of a plurality of exercise routines for any given physical malady. In any event, at least one exercise is typically prescribed and thus the present methodology call for at least one, but preferably a plurality of exercises, may be selected. Notably, the best-practice exercise or exercises are preferably selected by the physical therapy practitioner.

It is noted that if more than one best-practice exercise is selected, the preferred methodology may call for an additional step comprising the process of determining an exercise order. In other words, the physical therapy practitioner may order the given exercises so that the patient may more properly fulfill his or her physical therapy regimen because the order of exercises is oftentimes critical to proper fulfillment of a treatment plan. Preferably, the ordering of exercises may be achieved after the step of determining nomenclature for the representative best-practice excerpt. Should at least three best-practice exercises be selected during the step of selecting at least one best-practice exercise, it is contemplated that the step of determining exercise order may additionally comprise the process of determining an exercise grouping. In other words, the exercises may be grouped and ordered so that the patient may more properly benefit from the treatment plan as considered and prescribed by the physical therapy practitioner.

As earlier specified, given a clinic-based scenario, the present methodology requires the clinic (or physical therapy practitioner) to formally declare "at home" exercises, and in this way the specified methodology helps the clinic(s) or practitioners standardize with regard to the prescribed at home exercises. This standardization has two benefits. Firstly, because many therapists will have input into the final superset of exercises definition for the clinic, exchange of ideas and experiences will take place which focuses on why one exercise may be better then another exercise, assuming both exercises are intended to achieve the same result. The resulting superset, in essence, represents the clinic's "best practice" exercises. Secondly, it is common in many clinics for the patient to be treated by different therapists due to scheduling differences. Definition of the superset, which represents the clinic's best practices for at home exercises, increases the treatment compatibility among clinicians working at the same clinic. Having earlier compiled the digitized motion picture library, it is contemplated that the best-practice exercise, as selected by the physical therapy practitioner, is demonstrated by a representative best-practice exercise excerpt, which excerpt is included in the digitized motion picture library.

After selecting at least one best-practice exercise and noting that the same is demonstrated by a representative best-practice exercise excerpt, the excerpt is preferably reviewed by the physical therapy practitioner in an effort to come to agreement on the form and substance of the excerpt. In this regard, the physical therapy practitioner then preferably decides whether the representative best-practice exercise excerpt is endemic to or characteristic of the physical therapy practitioner. If the physical therapy practitioner is satisfied that the excerpt or clip adequately depicts the given prescriptive exercise according to the tenets of the practice (the excerpt is endemic to the physical therapy practitioner), the physical therapy practitioner then preferably determines nomenclature for the representative best-practice excerpt according to the tenets of the practice. Described another way, when the representative best-practice exercise excerpt is endemic to the physical therapy practitioner, the nomenclature is then preferably defined by the physical therapy practitioner.

The disclosed methodology may preferably comprise an additional step after the step of deciding whether the representative best-practice exercise excerpt is endemic to the physical therapy practitioner, which additional step comprises the process of developing and reviewing additional best-practice exercise excerpts should the representative best-practice exercise excerpt be deemed unsatisfactory (i.e. not endemic to the physical therapy practitioner). In this regard, it is preferred that additional best-practice excerpts be developed (by capturing additional digital motion picture type representations as requested by the practitioner) until the representative best-practice exercise excerpt is deemed endemic to the physical therapy practitioner. In other words, if the library does not have excerpts agreeable to the practicing physical therapist, further excerpts will be captured and archived so as to more effectively provide the practitioner with the visual exercise routines he or she deems endemic to the given practice.

After determining the practice-specific nomenclature for the representative best-practice exercise excerpt, digital versatile disc materials endemic to the physical therapy practitioner are then preferably developed. The digital versatile disc materials preferably comprise at least one digital versatile disc (DVD) and at least one navigation-comment sheet. The navigation-comment sheet is designed to provide the patient with patient-specific commentary deemed necessary to properly fulfill the prescribed physical therapy regimen. Notably, the representative best-practice exercise excerpt is placed upon the DVD for viewing. It will be recalled that typically, a plurality representative best-practice exercise excerpts are to be included in a home-based physical therapy regimen. Bearing in mind that any given home-based physical therapy regimen must include at least one representative best practice excerpt, it is here specified that the digital versatile disc materials include at least one, but preferably a plurality of representative best-practice exercise excerpts along with appropriate, practitioner defined nomenclature for each excerpts. Thus, it will be understood that the representative best-practice exercise excerpt(s) are identified in the digital versatile disc materials by the practitioner-defined nomenclature.

After determining the practice-specific nomenclature for the representative best-practice exercise excerpt and developing the digital versatile disc materials, the digital versatile disc materials are provided to the physical therapy practitioner. Thus, the practitioner warehouses, archives, or otherwise shelves the superset type digital disc materials for future delivery to patients. Having thus provided the practitioner with the developed digital versatile disc materials, the physical therapy practitioner is then in proper position to prescribe a home-based physical therapy regimen for a given patient, which regimen will necessarily include a select set of digital versatile disc materials. Thus, it will be understood that the home-based physical therapy regimen is prescribed for a patient by the physical therapy practitioner. In this last regard, it is noted that typically, the patient has direct contact with the physical therapy practitioner during a physical therapy appointment and it is during this physical therapy appointment that the home-based physical therapy regimen is planned and prescribed to the patient. During the physical therapy appointment or office visit, the select developed digital versatile disc materials may then be hand-delivered to the patient. The hand-delivery or immediate rendering of prescriptive visual motion picture type exercise routines is preferably in that physical therapy is typically time dependent. In other words, the benefits of physical therapy depend on how quickly the patient is able to implement his or her given physical therapy regimen. Having to wait for visual materials, as described by the '143 Publication, may well hinder the benefits of a given physical therapy regimen and thus immediate delivery of appropriate visual motion picture excerpts is believed to be superior to other methods known in the art. Thus, it is contemplated that the developed digital versatile disc materials may well serve to enhance compliance of the home-based physical therapy regimen.

As earlier noted, it is contemplated that the practitioner may be desirous of including various settings and/or auditory sensory information in the DVD representations. In this regard, the preferred methodology may further comprise representative best-practice exercise excerpts that comprise auditory sensory information endemic to the physical therapy practitioner, which auditory sensory information may include music, instructional language, tones, or other practice-specific auditory information as requested by the practitioner. After deciding whether the representative best-practice exercise excerpt(s) are endemic to the physical therapy practitioner, the disclosed methodology may thus comprise an additional step comprising the process of deciding whether the auditory sensory information is endemic to the physical therapy practitioner. If the auditory sensory information as included in the representative best-practice exercise excerpts is deemed unsatisfactory or not endemic to or uncharacteristic of a given practice, the methodology may comprise an additional step comprising the process of developing additional best-practice exercise excerpts as earlier specified so as to provide proper or endemic practice-specific auditory sensory information.

Thus, it will be understood that the present methodology provides to superset a library of video segments to a physical therapy patient via a physical therapy practitioner. This is distinctive to the art known to exist wherein patient-specific exercises are commonly ordered. The customized superset library of exercise video segments are designed to be practice-specific not patient-specific. The clinician or practitioner then provides the clinic's superset of videos on DVD along with at least one navigation-comment sheet to guide patient to appropriate exercise methods. Notably, DVD's inherently have different navigation methods than the Internet, CDs or printouts and thus the DVD medium is the preferred medium for the present methodology.

It will thus be noted that while certain art discloses customized presentation of work and exercise routine tailored to each individual patient, the present invention creates a collection of exercise video segments targeted for a given clinic's or practitioner's patients but not specific to any patient. The so-called "superset" approach introduces the need for navigation methodology. Certain art known to exist provides methodology for creating visual presentation over Internet, CD, and/or videotape. In contrast the present invention is DVD-based and requires a unique navigation method to insure that patients only view and perform the prescribed exercises.

While the above description contains much specificity, this specificity should not be construed as limitations on the scope of the invention, but rather as an exemplification of the invention. For example, it is contemplated that the present invention discloses a method for providing a physical therapy practitioner with practice-specific prescriptive exercise routine depictions, the practice-specific prescriptive exercise routine depictions for enhancing compliance of a home-based physical therapy regimen. Physical therapy philosophy, however, is dynamic and thus physical therapy philosophies and/or theories undergo revision from time to time. In other words, research continues to be undertaken and developments in the field are prevalent. In this regard, the practice of physical therapy may be viewed as dynamic in nature or character. In an effort to help account for the ever-developing field of physical therapy, it is contemplated that the methodology here disclosed may comprise an additional step after the step of providing the developed digital versatile disc materials to the physical therapy practitioner, the additional step comprising the process of updating the developed digital versatile disc materials. In this regard, certain correspondence with the practitioner would be undertaken so that the practitioner may provide the DVD provider with requests for DVD visual excerpt/auditory updates per the tenets of the given practice. Notably, the process of updating the developed digital versatile disc materials may thus be periodic in nature.

Accordingly, although the invention has been described by reference to a preferred embodiment, and two alterative embodiments, it is not intended that the novel assembly or apparatus be limited thereby, but that modifications thereof are intended to be included as falling within the broad scope and spirit of the foregoing disclosure, the following claims and the appended drawings.

We claim:

1. A method for enhancing compliance of a home-based physical therapy regimen, the method comprising the steps of:

compiling a digitized motion picture library, the digitized motion picture library comprising a plurality of visual best-practice exercise excerpts, each visual best-practice exercise excerpt visually demonstrating a prescriptive physical therapy exercise;

assessing home-based exercise prescriptions, the home-based exercise prescriptions being endemic to a physical therapy practitioner, the home-based exercise prescriptions comprising a plurality of best-practice exercises;

selecting at least one best-practice exercise, the best-practice exercise being selected by the physical therapy practitioner, the best-practice exercise being demonstrated by a representative best-practice exercise excerpt;

reviewing the representative best-practice exercise excerpt, the representative best-practice exercise being reviewed by the physical therapy practitioner;

deciding whether the representative best-practice exercise excerpt is endemic to the physical therapy practitioner;

determining nomenclature for the representative best-practice excerpt when the representative best-practice exercise excerpt is endemic to the physical therapy practitioner, the nomenclature being defined by the physical therapy practitioner;

developing digital versatile disc materials endemic to the physical therapy practitioner, the digital versatile disc materials comprising the representative best-practice exercise excerpt, the representative best-practice exercise excerpt being identified in the digital versatile disc materials by the nomenclature;

providing the developed digital versatile disc materials to the physical therapy practitioner;

prescribing a home-based physical therapy regimen, the home-based physical therapy regimen being prescribed for a patient by the physical therapy practitioner, the patient having contact with the physical therapy practitioner during a physical therapy appointment; and delivering a select set of developed digital versatile disc materials to the patient during the physical therapy appointment, the select set of developed digital versatile disc materials for enhancing compliance of the home-based physical therapy regimen.

2. The method of claim 1 wherein the method comprises an additional step after the step of deciding whether the representative best-practice exercise excerpt is endemic to the physical therapy practitioner, the additional step comprising the process of developing and reviewing additional best-practice exercise excerpts when the representative best-practice exercise excerpt is not endemic to the physical therapy practitioner, the additional best-practice excerpts being developed until the representative best-practice exercise excerpt is deemed endemic to the physical therapy practitioner.

3. The method of claim 1 wherein the representative best practice exercise excerpt comprises auditory sensory information, the auditory sensory information being endemic to the physical therapy practitioner.

4. The method of claim 3 wherein the auditory sensory information comprises instructional language, the instructional language for enhancing compliance of the home-based physical therapy regimen.

5. The method of claim 4 wherein the method comprises an additional step after the step of deciding whether the representative best-practice exercise excerpt is endemic to the physical therapy practitioner, the additional step comprising the process of deciding whether the auditory sensory information is endemic to the physical therapy practitioner.

6. The method of claim 5 wherein the method comprises an additional step after the process of deciding whether the auditory sensory information is endemic to the physical therapy practitioner, the additional step comprising the process of developing additional best-practice exercise excerpts when the auditory sensory information is not endemic to the physical therapy practitioner.

7. The method of claim 1 wherein at least two best-practice exercises are selected during the step of selecting at least one best practice exercise, the method comprising an additional step after the step of determining nomenclature for the representative best-practice excerpt, the additional step comprising the process of determining an exercise order.

8. The method of claim 7 wherein the at least three best practice exercises are selected during the step of selecting at least one best practice exercise, the step of determining exercise order comprising the process of determining an exercise grouping.

9. The method of claim 1 wherein the digital versatile disc materials comprise at least one digital versatile disc and at least one navigation-comment sheet.

10. The method of claim 9 wherein the step of prescribing a home-based physical therapy regimen comprises the processes of prescribing patient-specific exercises and recording patient-specific comments on the navigation-comment sheet.

11. The method of claim 1 wherein the method comprises an additional step after the step of providing the developed digital versatile disc materials to the physical therapy practitioner, the additional step comprising the process of updating the developed digital versatile disc materials, the process of updating the developed digital versatile disc materials being periodic.

12. A method for providing a physical therapy practitioner with practice-specific prescriptive exercise routine depictions, the practice-specific prescriptive exercise routine depictions for enhancing compliance of a home-based physical therapy regimen, the method comprising the steps of:

compiling a digitized motion picture library, the digitized motion picture library comprising a plurality of visual best-practice exercise excerpts, each visual best-practice exercise excerpt visually demonstrating a prescriptive physical therapy exercise;

assessing home-based exercise prescriptions, the home-based exercise prescriptions being endemic to a physical therapy practitioner, the home-based exercise prescriptions comprising a plurality of best-practice exercises;

selecting at least one best-practice exercise, the best-practice exercise being selected by the physical therapy practitioner, the best-practice exercise being demonstrated by a representative best-practice exercise excerpt;

reviewing the representative best-practice exercise excerpt, the representative best-practice exercise being reviewed by the physical therapy practitioner;

deciding whether the representative best-practice exercise excerpt is endemic to the physical therapy practitioner;

developing digital versatile disc materials endemic to the physical therapy practitioner, the digital versatile disc materials comprising the representative best-practice exercise excerpt;

providing the developed digital versatile disc materials to the physical therapy practitioner;

prescribing a home-based physical therapy regimen, the home-based physical therapy regimen being prescribed for a patient by the physical therapy practitioner, the patient having contact with the physical therapy practitioner during a physical therapy appointment; and delivering a select set of the developed digital versatile disc materials to the patient during the physical therapy appointment, the select set of developed digital versatile disc materials for enhancing compliance of the home-based physical therapy regimen.

13. The method of claim 12 wherein the method comprises an additional step after the step of deciding whether the representative best-practice exercise excerpt is endemic to the physical therapy practitioner, the additional step comprising the process of determining nomenclature for the representative best-practice excerpt when the representative best-practice exercise excerpt is endemic to the physical therapy practitioner, the nomenclature being defined by the physical therapy practitioner, the representative best-practice exercise excerpt being identified in the digital versatile disc materials by the nomenclature.

14. The method of claim 12 wherein the method comprises an additional step after the step of deciding whether the representative best-practice exercise excerpt is endemic to the physical therapy practitioner, the additional step comprising the process of developing and reviewing additional best-practice exercise excerpts when the representative best-practice exercise excerpt is not endemic to the physical therapy practitioner, the additional best-practice excerpts being developed and reviewed until the representative best-practice exercise excerpt is deemed endemic to the physical therapy practitioner.

15. The method of claim 13 wherein at least two best-practice exercises are selected during the step of selecting at least one best-practice exercise, the method comprising an additional step after the process of determining nomenclature for the representative best-practice excerpt, the additional step comprising the process of determining an exercise order.

16. The method of claim 12 wherein the at least three best-practice exercises are selected during the step of selecting at least one best-practice exercise, the step of determining exercise order comprising the process of determining an exercise grouping.

17. The method of claim 12 wherein the digital versatile disc materials comprise at least one digital versatile disc and at least one navigation-comment sheet.

18. The method of claim 17 wherein the step of prescribing a home-based physical therapy regimen comprises the processes of prescribing patient-specific exercises and recording patient-specific comments on the navigation-comment sheet.

19. A method for providing a physical therapy practitioner with practice-specific prescriptive exercise routine depictions, the practice-specific prescriptive exercise routine depictions for enhancing compliance of a home-based physical therapy regimen, the method comprising the steps of:
  assessing home-based exercise prescriptions, the home-based exercise prescriptions being endemic to a physical therapy practitioner, the home-based exercise prescriptions comprising a plurality of best-practice exercises;
  selecting at least one best-practice exercise, the best-practice exercise being selected by the physical therapy practitioner;
  selecting a representative best-practice exercise excerpt, the representative best-practice exercise excerpt being selected from a compiled digitized motion picture library, the digitized motion picture library comprising a plurality of visual best-practice exercise excerpts;
  deciding whether the representative best-practice exercise excerpt is endemic to the physical therapy practitioner;
  developing digital versatile disc materials endemic to the physical therapy practitioner, the digital versatile disc materials comprising the representative best-practice exercise excerpt;
  providing the developed digital versatile disc materials to the physical therapy practitioner;
  prescribing a home-based physical therapy regimen, the home-based physical therapy regimen being prescribed for a patient by the physical therapy practitioner, the patient having contact with the physical therapy practitioner during a physical therapy appointment; and
  delivering a select set of the developed digital versatile disc materials to the patient during the physical therapy appointment, the select set of developed digital versatile disc materials for enhancing compliance of the home-based physical therapy regimen.

20. The method of claim 19 wherein the step of selecting a representative best-practice exercise excerpt is repeated after the step of deciding whether the representative best-practice exercise excerpt is endemic to the physical therapy practitioner until the selected representative best-practice exercise excerpt is endemic to the physical therapy practitioner.

21. The method of claim 19 wherein the method comprises an additional step after the step of deciding whether the representative best-practice exercise excerpt is endemic to the physical therapy practitioner, the additional step comprising the process of developing and reviewing additional best-practice exercise excerpts when the representative best-practice exercise excerpt is not endemic to the physical therapy practitioner, the additional best-practice excerpts being developed and reviewed until the representative best-practice exercise excerpt is deemed endemic to the physical therapy practitioner.

22. The method of claim 19 wherein the method comprises an additional step after the step of deciding whether the representative best-practice exercise excerpt is endemic to the physical therapy practitioner, the additional step comprising the process of determining nomenclature for the representative best-practice excerpt when the representative best-practice exercise excerpt is endemic to the physical therapy practitioner, the nomenclature being defined by the physical therapy practitioner, the representative best-practice exercise excerpt being identified in the digital versatile disc materials by the nomenclature.

* * * * *